United States Patent [19]
Renfrew et al.

[11] 4,182,720
[45] Jan. 8, 1980

[54] PROCESS FOR THE PREPARATION OF HOMOGENTISIC LACTONE

[75] Inventors: Andrew H. M. Renfrew; Stephen B. Bostock, both of Blackley, England

[73] Assignee: Imperial Chemical Industries Limited, London, England

[21] Appl. No.: 926,323

[22] Filed: Jul. 20, 1978

[30] Foreign Application Priority Data

Aug. 26, 1977 [GB] United Kingdom ............... 35931/77

[51] Int. Cl.$^2$ ........................................... C07D 307/83
[52] U.S. Cl. ............................................. 260/343.3 R
[58] Field of Search ................................ 260/343.3 R

[56] References Cited
U.S. PATENT DOCUMENTS 3,862,133   1/1975   Layer ........................... 260/343.3 R

OTHER PUBLICATIONS

Smith et. al. Jour. Am. Chem. Soc. vol. 58. 1936. pp. 629–635.

Primary Examiner—Natalie Trousof
Assistant Examiner—Jane T. Fan
Attorney, Agent, or Firm—Cushman, Darby & Cushman

[57] ABSTRACT

Process for the preparation of homogentisic lactone by reacting hydroquinone with a di(lower alkyl) chloro (or bromo) malonate and an alkali metal lower alkoxide to give an alkali metal 3-carbo(loweralkoxy)-5-hydroxy-2-oxidobenzo[b]furan which is subsequently decarboxylated by treatment with a strong mineral acid to give homogentisic lactone. The latter is readily converted into homogentisic acid by conventional means.

5 Claims, No Drawings

PROCESS FOR THE PREPARATION OF HOMOGENTISIC LACTONE

This invention relates to a chemical process and more particularly to a process for the preparation of homogentisic lactone. Homogentisic lactone is a precursor of homogentisic acid (2,5-dihydroxyphenylacetic acid), which is of value as a photographic dye developer and as an intermediate in the manufacture of dyestuffs and pharmaceuticals.

The best method known for preparing homogentisic acid appears to be that described in J. Biol. Chem. 179, 365 (1949), in which 1,4-dimethoxybenzene is reacted with acetyl chloride in the presence of aluminum chloride to give 2,5-dimethoxyacetophenone, the latter is reacted with sulphur in morpholine to give 2,5-dimethoxyphenylacetic acid, which on demethylation with hydrobromic acid gives homogentisic lactone, ring-opening of which gives the desired acid.

It has now been found that homogentisic lactone, and thus the acid, can be prepared by a much simpler route which avoids using the Friedel-Crafts reaction and the sulphur/morpholine conversion of —$COCH_3$ into —$CH_2CO_2H$.

According to the present invention there is provided a process for the manufacture of homogentisic lactone which comprises the steps of:

(i) reacting hydroquinone with a di(lower alkyl) chloromalonate or bromomalonate and an alkali metal lower alkoxide to give an alkali metal 3-carbo(lower alkoxy)-5-hydroxy-2-oxidobenzo[b]furan; and (ii) treatment of the alkali metal 3-carbo(lower alkoxy)-5-hydroxy-2-oxidobenzo[b]furan from step (1) with a strong mineral acid to give homogentisic lactone.

The terms "lower alkyl" and "lower alkoxy" in this specification mean alkyl and alkoxy groups respectively which contain from 1 to 4 carbon atoms. The alkali metal 3-carbo(lower alkoxy)-5-hydroxy-2-oxidobenzo[b]furan is named in this specification and the appended claims according to the Ring Index, Second Edition, page 173, published by the American Chemical Society.

The first step of the above-defined process is conveniently carried out in a substantially anhydrous alcohol as solvent, preferably the same alcohol from which the alkali metal lower alkoxide is derived. Suitable alcohols are, for example, methanol and ethanol. This first step of the process is preferably carried out under an inert atmosphere, for example, nitrogen. The reaction is mildly exothermic and proceeds at normal room temperatures. To ensure completion of the reaction the reaction mixture may be heated, conveniently at the reflux temperature of the solvent. The product of this first step, an alkali metal 3-carbo(lower alkoxy)-5-hydroxy-2-oxidobenzo[b]furan contaminated with sodium chloride or sodium bromide, is isolated by filtration and is preferably washed with fresh alcoholic solvent before drying.

The strong mineral acid used in step (2) of the process may be, for example, orthophosphoric acid. The reaction involves evolution of carbon dioxide from decarboxylation of the intermediate from step (1), and to avoid possible difficulties due to foaming an anti-foaming agent, for example a silicone anti-foam, may be added to the reaction mixture. Step (2) is carried out at an elevated temperature, for example, up to 90° C. or even higher if desired. After the decarboxylation is complete the homogentisic lactone may be isolated by drowning the reaction mixture into ice, or ice and water, the precipitated product being collected, washed acid-free with the minimum of ice-cold water, and dried. If desired the lactone so obtained may be purified by recrystallisation from methanol.

The homogentisic lactone so obtained may then be converted into homogentisic acid by methods known from the prior art, for example, by treating the lactone with an aqueous solution of an alkali metal hydroxide to open the lactone ring and give the alkali metal salt of homogentisic acid, followed by acidification of the solution so obtained to give homogentisic acid itself.

The invention is illustrated but not limited by the following Example in which parts and percentages are by weight.

EXAMPLE

Sodium metal (4.6 parts) is dissolved in absolute methanol (180 parts, water content <0.05%) and the solution is cooled to 30° C. Hydroquinone (22 parts) is added, under nitrogen, and the suspension is stirred for 5 minutes to give a pale orange solution. Finally, dimethyl chloromalonate (17.4 parts; 96% strength) is added all at once at 25° C. A dark green colour is produced followed by an exotherm to 37° C., and after 5 minutes a grey solid begins to separate. Stirring is continued for 2 hours and the suspension is then heated under reflux for a further 2.½ hours. Methanol (120 parts) is distilled off, maintaining the nitrogen atmosphere, glacial acetic acid (5 parts) is added to the thick suspension and the reaction mass is chilled in ice for 30 minutes. The solid product is collected by filtration, washed with two portions (each of 16 parts) of absolute methanol, and dried to give 20 parts of sodium 3-carbomethoxy-5-hydroxy-2-oxidobenzo[b]furan contaminated with sodium chloride. The solid is ground and shown by analysis to contain 5 parts of sodium chloride. The yield of intermediate product is therefore 15 parts (65% of theoretical yield).

To orthophosphoric acid (60 parts; 90%) at 90° C. is added portionwise, during 30 minutes, with stirring, sodium 3-carbomethoxy-5-hydroxy-2-oxidobenzo[b]furan (13 parts 75.8% pure). A trace of silicone anti-foam is added to the reaction mixture to moderate the vigorous effervescence which ensues. After 4 hours at 90° C. the reaction mixture is drowned into ice (40 parts), the solid which precipitates is filtered off, washed acid-free with the minimum amount of ice-cold water and dried to give homogentisic lactone (5.1 parts; 80%). Crystallisation of the product from methanol gives light tan-coloured needles, m.p. 189° C.

We claim:

1. A process for the manufacture of homogentisic lactone which comprises the steps of (i) reacting hydroquinone with a di-(lower alkyl) chloromalonate or bromomalonate and an alkali metal lower alkoxide to give an alkali metal 3-carbo(lower alkoxy)-5-hydroxy-2-oxidobenzo[b]furan, and (ii) treatment of the product obtained from step (i) with a strong mineral acid to give homogentisic lactone.

2. A process as claimed in claim 1 in which step (i) is carried out in a substantially anhydrous alcohol as solvent.

3. A process as claimed in claim 2 wherein the alcohol is the same as that from which the alkali metal alkoxide is derived.

4. A process as claimed in claim 1 wherein the process is carried out under an inert atmosphere.

5. A process as claimed in claim 1 wherein step (ii) is carried out in the presence of an antifoaming agent.

* * * * *